United States Patent [19]

Habib et al.

[11] 4,361,706

[45] Nov. 30, 1982

[54] PROCESS FOR PREPARING ALDEHYDES

[75] Inventors: Mohammad M. Habib, Allison Park; Wayne R. Pretzer, Gibsonia, both of Pa.

[73] Assignee: Gulf Research & Development Company, Pittsburgh, Pa.

[21] Appl. No.: 289,404

[22] Filed: Aug. 3, 1981

[51] Int. Cl.[3] .............................................. C07C 45/49
[52] U.S. Cl. .................................. 568/487; 568/454; 568/882; 568/909
[58] Field of Search ............... 568/487, 454, 882, 496

[56] References Cited

U.S. PATENT DOCUMENTS

| | | | |
|---|---|---|---|
| 4,151,208 | 4/1979 | Pretzer et al. | 568/487 |
| 4,190,729 | 2/1980 | Forster | 568/487 |
| 4,239,704 | 12/1980 | Pretzer et al. | 568/487 |
| 4,239,705 | 12/1980 | Pretzer et al. | 568/487 |
| 4,262,154 | 4/1981 | Gane et al. | 568/487 |
| 4,293,718 | 10/1981 | Gauthier-Lafaye et al. | 568/487 |

*Primary Examiner*—Werren B. Lone
*Attorney, Agent, or Firm*—Deane E. Keith; Forrest D. Stine; Joseph J. Carducci

[57] ABSTRACT

A process for selectively producing aldehydes, particularly acetaldehyde, which comprises introducing into a reaction zone (1) methanol, (2) carbon monoxide, (3) hydrogen, (4) cobalt, (5) iodine and (6) a ligand containing atoms from Group VB of the Periodic Table separated by a sterically constrained carbon-carbon bond and then subjecting the contents of said reaction zone to an elevated temperature and an elevated pressure for a time sufficient to convert methanol to said aldehydes.

35 Claims, No Drawings

PROCESS FOR PREPARING ALDEHYDES

BACKGROUND OF THE INVENTION

1. Field of the Invention

This invention is directed to a process for selectively producing aldehydes, particularly acetaldehyde, which comprises introducing into a reaction zone (1) methanol, (2) carbon monoxide, (3) hydrogen, (4) cobalt, (5) iodine and (6) a ligand containing atoms from Group VB of the Periodic Table separated by a sterically constrained carbon-carbon bond and then subjecting the contents of said reaction zone to an elevated temperature and an elevated pressure for a time sufficient to convert methanol to said aldehydes.

2. Description of the Invention

In European Patent Application No. 79302053.8, filed in the names of B. R. Gane and D. G. Stewart and published on Apr. 30, 1980, it is disclosed that when methanol is reacted with synthesis gas in the presence of a catalyst comprising (a) cobalt, (b) an iodide or a bromide and (c) a polydentate ligand, wherein the donor atoms are exclusively phosphorus, the product obtained will contain a substantial proportion of ethanol. When the polydentate ligand used is one wherein at least one of the donor atoms is phosphorus and another is arsenic, it is alleged by Gane et al that the product will contain a mixture of ethanol and acetaldehyde.

SUMMARY OF THE INVENTION

We have found that if we introduce into a reaction zone (1) methanol, (2) carbon monoxide, (3) hydrogen, (4) cobalt, (5) iodine and (6) a ligand containing atoms from Group VB of the Periodic Table separated by a sterically constrained carbon-carbon bond, while controlling the proportion of the reaction components and the reaction parameters, we can obtain a reaction product predominating in aldehydes, including compounds convertible thereto, particularly acetaldehyde. By "compounds convertible thereto" we mean to include acetals, such as dimethyl acetal. In general the reaction product will contain at least about 30 weight percent, especially from about 35 to about 85 weight percent, of aldehydes and compounds convertible thereto. The acetaldehyde content of the reaction product will be at least about 25 weight percent, especially about 27 to about 75 weight percent. At the same time, the alcohol content of the reaction product, including compounds convertible thereto, will be very small. By "compounds convertible thereto", in the latter instance, we mean to include acetates, such as ethyl acetate. In general the reaction product will contain less than about 23 weight percent of alcohols and compounds convertible thereto, but more often from about two to about ten weight percent of alcohols and compounds convertible thereto. As to the ethanol content of the reaction product it will be less than about 18 weight percent, but more often in the range of about 0 to about seven weight percent. The compounds referred to above that can be converted to aldehydes or alcohols can be converted thereto by any known or suitable process, for example, by hydrolysis, that is, contacting a precursor thereof with water, with or without an acid (sulfuric) or a basic (sodium hydroxide) catalyst.

As noted, the ligand used herein contains atoms from Group VB of the Periodic Table. By "Group VB atoms" we mean to include nitrogen, phosphorus and arsenic. By a "sterically constrained carbon-carbon bond" we mean to include a carbon-carbon bond of an organic divalent radical in which the radical centers are located on adjacent carbon atoms and in which the bond axis of these adjacent carbon atoms is inhibited from rotating by either bond unsaturation or by their incorporation into an alicyclic ring system. By bond unsaturation we mean to include an alkylene bond, such as

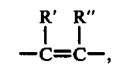

and an arylene bond, such as

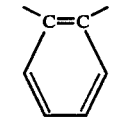

or an acetylenic bond such as —C≡C— wherein any of the above-defined R substituents can be hydrogen, a hydrocarbyl, such as defined hereinafter, a halogen, such as chlorine or bromine, a sulfur-containing substituent, such as a sulfonato group, a nitrogen-containing substituent, such as a nitro group or an amino group, an oxygen-containing substituent, such as a hydroxyl group, etc. By "alicyclic ring system", we mean to include an aliphatic ring system comprising a three- to eight-membered ring, such as

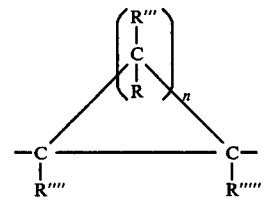

wherein n=1, 2, 3, 4, 5, or 6 and any of the above-defined R groups can be similar to R' and R".

Especially preferred ligands for use herein can be defined by the following formula:

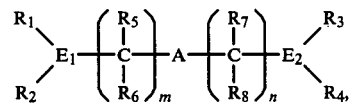

wherein $R_1$, $R_2$, $R_3$ and $R_4$ are either alike or different members selected from the group consisting of alkyl radicals having from one to 24 carbon atoms, preferably from two to 10 carbon atoms; aryl radicals having from six to 20 carbon atoms, preferably from six to 10 carbon atoms; alkenyl radicals having from two to 30 carbon atoms, preferably from two to 20 carbon atoms; cycloalkyl radicals having from three to 40 carbon atoms, preferably from three to 30 carbon atoms; and aralkyl and alkaryl radicals having from six to 40 carbon atoms, preferably from six to 30 carbon atoms; preferably aryl or alkyl; $R_5$, $R_6$, $R_7$ and $R_8$ are either alike or different members selected from $R_1$, $R_2$, $R_3$ and $R_4$, defined above, and hydrogen, preferably hydrogen or alkyl; $E_1$ and $E_2$ the same or different, can be phosphorus or arsenic, preferably with $E_1$ being phosphorus and $E_2$ being arsenic, most preferably with each of $E_1$ and $E_2$ being phosphorus; and m and n being integers ranging from 0 to 2, preferably from 0 to 1, provided that m+n=0-4, preferably 0-2; and A can be an organic divalent radical in which the radical centers are located on adjacent carbon atoms and in which the bond axis of these adjacent carbon atoms is inhibited from rotating by bond unsaturation, e.g., aromatic, heterocyclic, olefinic, or acetylenic, or by their incorporation into an alicyclic ring system comprising a three- to eight-membered ring. When A is an alicyclic group or includes an alkylene linkage, the bidentate ligand includes cis-type and trans-type steric isomers. In the present invention, both isomers can be used. Included among the ligands that can be employed herein, some of which are believed to be novel, are those defined below in Table I, referring to the structural formula hereinabove defined.

TABLE I

| | $R_1$ | $R_2$ | $R_3$ | $R_4$ | $R_5$ | $R_6$ | $R_7$ | $R_8$ | $E_1$ | $E_2$ | A | m | n |
|---|---|---|---|---|---|---|---|---|---|---|---|---|---|
| 1. | Phenyl | Phenyl | Phenyl | Phenyl | — | — | — | — | P | P | H H<br>—C=C— | 0 | 0 |
| 2. | Phenyl | Phenyl | Phenyl | Phenyl | — | — | — | — | P | P |  | 0 | 0 |
| 3. | Phenyl | Phenyl | Phenyl | Phenyl | H | H | H | H | P | P | " | 1 | 1 |
| 4. | Phenyl | Phenyl | Phenyl | Phenyl | $CH_3$ | H | H | H | P | P | " | 1 | 1 |
| 5. | Phenyl | Phenyl | Phenyl | Phenyl | $CH_3$ | H | $CH_3$ | H | P | P | " | 2 | 2 |
| 6. | Phenyl | Phenyl | Ethyl | Ethyl | — | — | — | — | P | P | " | 0 | 0 |
| 7. | Phenyl | Phenyl | Ethyl | Ethyl | H | $CH_3$ | H | H | P | As | " | 1 | 1 |
| 8. | Phenyl | Phenyl | Phenyl | Phenyl | — | — | — | — | P | P |  | 0 | 0 |
| 9. | Phenyl | Phenyl | Phenyl | Phenyl | — | — | — | — | P | P |  | 0 | 0 |
| 10. | Phenyl | Phenyl | Phenyl | Phenyl | — | — | — | — | P | P |  | 0 | 0 |
| 11. | Phenyl | Phenyl | Phenyl | Phenyl | — | — | — | — | P | P |  | 0 | 0 |
| 12. | Phenyl | Phenyl | Ethyl | Ethyl | H | H | H | H | P | P |  | 1 | 1 |
| 13. | Phenyl | Phenyl | Phenyl | Phenyl | H | H | H | H | P | P |  | 0 | 0 |
| 14. | Phenyl | Phenyl | Phenyl | Phenyl | — | — | — | — | P | P | —C≡C— | 0 | 0 |
| 15. | Phenyl | Phenyl | Phenyl | Phenyl | H | H | H | H | P | P |  | 1 | 1 |

Any source of iodine which is capable of dissociating, that is, ionizing to form free iodide ions in the reaction medium can be used in the present invention. Illustrative examples of iodine compounds especially suitable for use herein include iodine, potassium iodide, calcium iodide, sodium iodide, lithium iodide, aluminum iodide, bismuth iodide, hydrogen iodide, methyl iodide, ethyl iodide, etc., and mixtures thereof.

The cobalt entity suitable for use herein an be defined as being a cobalt carbonyl, a hydrido cobalt carbonyl or a cobalt-containing compound convertible to a cobalt carbonyl or a hydrido cobalt carbonyl. By "cobalt carbonyl" we intended to define a compound containing only cobalt and carbon monoxide, such as $Co_2(CO)_8$ or $Co_4(CO)_{12}$. By "hydrido cobalt carbonyl" we intended to define a compound containing only cobalt, carbon monoxide and hydrogen, such as $HCo(CO)_4$. By "cobalt-containing material convertible to a cobalt carbonyl or a hydrido cobalt carbonyl" we intend to define any material which when mixed with hexane and subjected to 4000 pounds per square inch gauge (27.6 MPa) in an atmosphere containing hydrogen and carbon monoxide in a molar ratio of 1:1 at 150° to 200° C. for a period of three hours will result in the formation of a cobalt carbonyl, a hydrido cobalt carbonyl or mixtures thereof. Specific examples of a cobalt-containing material so convertible to a cobalt carbonyl or a hydrido cobalt carbonyl include cobalt(II)sulfate, cobalt oxide($Co_3O_4$), cobalt(II)tetrafluoroborate, cobalt(II)acetate, cobalt((II)oxalate, cobalt(II)propionate, cobalt(II)octoate, cobalt(II)butyrate, cobalt(II)benzoate, cobalt(II)valerate, cobalt(II)formate, cobalt(II)cyclohexanebutyrate, cobalt(II)2-ethyl-hexaoate, cobalt(II)gluconate, cobalt(II)lactate, cobalt(II)naphthenate, cobalt(II)oleate, cobalt(II)citrate, cobalt(II)acetylacetonate, etc.

The relative amounts of carbon monoxide and hydrogen employed can be varied over a wide range. However, in general, the molar ratio of carbon monoxide to hydrogen is from about 2:1 to about 1:2, preferably about 1.5:1 to about 1:1.5, but most preferably about 1.25:1 to about 1:1.25. Compounds or reaction mixtures which give rise to the formation of carbon monoxide and hydrogen under the reaction conditions defined herein can be used instead of mixtures comprising carbon monoxide and hydrogen which are used in the preferred embodiments of this invention.

In order to obtain a product herein that predominates in aldehydes, particularly acetaldehyde, the amount of cobalt employed relative to the ligand and to iodine is critical. Thus, the molar ratio of cobalt based on the element cobalt, to the ligand must be in the range of about 1:2 to about 7:1, preferably about 1:1.5 to about 4:1. The molar ratio of cobalt, based on the element cobalt, to iodine, based on the element iodine, must be in the range of about 1:1.15 to 1:15, preferably about 1:1.25 to about 1:5. Based on the methanol introduced into the system, the weight percent of combined cobalt and iodine, in their elemental form, can range from about 0.01 to about 10 percent, preferably from about 0.1 to about five percent.

The process herein can be carried out either in a batch operation or by passing the reactants continuously through a reaction zone. In each case the reactor is provided with agitation means and the pressure is maintained therein by the addition of hydrogen and carbon monoxide, or compounds producing hydrogen and carbon monoxide, as required. In order to facilitate the introduction of the phosphorus-containing ligand and the cobalt and iodine entities into the reaction zone and/or to facilitate recovery of the components of the reaction herein, they can be dissolved in an inert solvent, such as ethylene glycol, diethylene glycol monomethyl ether, acetone, sulfolanes, such as tetramethylene sulfone, lactones, such as γ-butyrolactone and ε-caprolactone, etc.

In the reaction zone the contents thereof are maintained at an elevated temperature and at an elevated critical pressure for a time sufficient to convert methanol to the desired aldehydes. The total pressure (based on hydrogen, carbon monoxide and any produced gases) must be at least about 2200 pounds per square inch gauge (15.02 MPa) but need not be in excess of about 10,000 pounds per square inch gauge (68.30 MPa). Especially desirable are pressures in the range of about 2500 pounds per square inch gauge (17.07 MPa) to about 7500 pounds per square inch gauge (51.19 MPa). Temperatures which are suitable for use herein are those temperatures which initiate a reaction between the reactants herein to selectively produce aldehydes, generally from about 150° to about 250° C., preferably from about 170° to 220° C. The reaction is conducted for a time period sufficient to convert methanol to aldehydes, normally from about five minutes to about five hours, preferably from about ten minutes to about 2.5 hours.

Recovery of the desired aldehydes, for example acetaldehyde, from the reaction product can be effected in any convenient or conventional manner, for example, by distillation, at ambient pressure and about 21° C. The components will distill off in the following sequence for the desired recovery: acetaldehyde, propionaldehyde, methyl acetate, methanol, butyraldehyde, ethyl acetate, ethanol, etc.

DESCRIPTION OF PREFERRED EMBODIMENTS

A series of runs was carried out as follows. In each of Runs Nos. 1, 3, 4, and 7 there was charged into a 300 cc. stainless steel autoclave, equipped with agitation means, 100 milliliters of methanol, 10 millimols of cobaltous acetylacetonate, 10 millimols of iodine ($I_2$) and five millimols of a specific ligand containing atoms from Group VB of the Periodic Table separated by an unsaturated linkage. These ligands were as follows: cis-bis(1,2-diphenylphosphino)ethylene (Run No. 1), bis(1,2-diphenylphosphino)benzene (Run No. 3), bis-alpha-alpha'-diphenylphosphino)-0-xylene (Run No. 4) and bis(diphenylphosphino)acetylene (Run No. 7). The reactor was next purged twice with nitrogen gas and then pressurized with carbo monoxide and hydrogen to a pressure of about half the desired reaction pressure. The system was then heated to a temperature of 200° C. and the pressure was adjusted to the reaction pressure, while maintaining selected molar ratios of carbon monoxide to hydrogen in the reaction zone, and such pressure was maintained throughout the reaction period. At the end of the reaction period the reactor contents were cooled by an internal cooling coil to about −75° C. The reactor was vented through a dry gas meter and a gas sample was taken for a mass spectral analysis and the liquid product was then analyzed by gas chromatography. The data obtained are set forth below in Tables II and III.

TABLE II

| Run No. | $R_1, R_2, R_3, R_4$ | m | n | $R_5, R_6, R_7, R_8$ | A | Co:Ligand[a] Molar Ratio | Co:I Molar Ratio | $CO:H_2$ | Pressure PSIG (MPa) | Reaction, Time Hours | Percent[b] MeOH Conversion |
|---|---|---|---|---|---|---|---|---|---|---|---|
| I | Phenyl | 0 | 0 | Hydrogen | $-\underset{H}{C}=\underset{H}{C}-$ | 2:1 | 0.5:1 | 1:1 | 4000(27.3) | 1.0 | 92.0 |
| II | Phenyl | 0 | 0 | Hydrogen | $-\underset{H}{\overset{H}{C}}=\underset{H}{\overset{H}{C}}-$ | 4:1[p] | 0.5:1 | 1:1 | 4000(27.3) | 1.0 | 93.0 |
| III | Phenyl | 0 | 0 | Hydrogen | (phenylene -C=C-) | 2:1 | 0.5:1 | 1:1 | 4000(27.3) | 1.0 | 93.0 |
| IV | Phenyl | 1 | 1 | Hydrogen | (phenylene -C=C-) | 2:1 | 0.5:1 | 1:1 | 4000(27.3) | 1.0 | 79.7 |
| V | Phenyl | 0 | 0 | Hydrogen | (phenylene C=C) | 2:1[p] | 0.5:1 | 1.5:1 | 4000(27.3) | 1.0 | 90.0 |
| VI | Phenyl | 0 | 0 | Hydrogen | (phenylene C=C) | 2:1[p] | 0.8:1 | 1:1 | 4000(27.3) | 1.0 | 86.0 |
| VII | Phenyl | 0 | 0 | Hydrogen | $-C\equiv C-$ | 2:1 | 0.5:1 | 1:1 | 4000(27.3) | 1.0 | 61.7 |

[a] 

[b] Methanol

[p] Cobalt carbonyl (5.0 mmol) was used.

TABLE III

| Run No. | $Me_2O$[c] | HAc[d] | MeF[e] | EtOH[f] | $Et(OMe)_2$[g] | EtCHO[h] | MeOAc[i] | PrCHO[j] | EtOAc[k] | HOAc[l] | Others[m] | Total Weight Percent Aldehydes[n] | Total Weight Percent Alcohols[o] |
|---|---|---|---|---|---|---|---|---|---|---|---|---|---|
| I | 3.7 | 53.8 | 0.6 | 5.5 | 0 | 0.4 | 11.5 | 17.4 | 3.8 | 0 | 3.2 | 72.6 | 5.6 |
| II | 4.8 | 41.0 | 0.2 | 0.8 | 0.8 | 0.2 | 19.7 | 19.7 | 6.3 | 3.3 | 3.2 | 64.1 | 7.9 |
| III | 1.9 | 51.2 | 0.7 | 0.5 | 3.4 | 0.4 | 15.4 | 17.3 | 6.1 | 0 | 2.7 | 69.7 | 6.6 |
| IV | 6.5 | 28.0 | 0.1 | 1.0 | 2.5 | 2.8 | 24.6 | 7.0 | 2.5 | 0 | 24.9 | 60.3 | 8.5 |
| V | 7.1 | 43.7 | 0.6 | 17.0 | 3.7 | 0.6 | 8.4 | 7.8 | 5.9 | 2.2 | 3.0 | 56.4 | 22.9 |
| VI | 2.0 | 43.7 | 0.5 | 9.0 | 1.3 | 1.0 | 19.8 | 12.7 | 8.2 | 1.0 | 0.9 | 58.2 | 17.2 |
| VII | 11.5 | 28.9 | 0 | 0 | 1.2 | 0.6 | 27.4 | 5.7 | 1.7 | 2.2 | 20.7 | 53.1 | 5.8 |

[c] Dimethyl ether $CH_3OCH_3$
[d] Acetaldehyde $CH_3CHO$
[e] Methyl formate $HCOOCH_3$
[f] Ethanol $C_2H_5OH$
[g] Dimethyl acetal $CH_3CH(OCH_3)_2$
[h] Propanal $C_2H_5CHO$
[i] Methyl acetate $CH_3COOCH_3$
[j] Butanal $C_3H_7CHO$
[k] Ethyl acetate $CH_3COOC_2H_5$
[l] Acetic acid $CH_3COOH$
[m] Mixtures of 1,1-dimethoxy ethane, 1,1-dimethoxy butane, 1,1-diethoxy ethane, diethylether, crotonaldehyde and other aldehyde condensation products
[n] Aldehydes + materials convertible to aldehydes, for example, by hydrolysis
[o] Alcohols + materials convertible to alcohols, for example, by hydrolysis The data in the above Tables clearly show that when ligands defined herein are used in the claimed process a product is obtained containing the desired amounts of aldehydes, including the desired amounts of acetaldehyde.

Obviously, many modifications and variations of the invention, as hereinabove set forth, can be made without departing from the spirit and scope thereof, and therefore only such limitations should be imposed as are indicated in the appended claims.

We claim:

1. A process for selectively producing aldehydes which comprises introducing into a reaction zone (1) methanol, (2) carbon monoxide, (3) hydrogen, (4) cobalt, (5) iodine and (6) a ligand containing phosphorus atoms separated by a sterically constrained carbon-carbon bond, the molar ratio of carbon monoxide to hydrogen being in the range of about 2:1 to about 1:2, the molar ratio of cobalt to said ligand being in the range of about 1:2 to about 7:1, the molar ratio of cobalt to iodine being in the range of about 1:1.15 to about 1:15, and the weight percent of combined cobalt and iodine, based on the methanol, being in the range of about 0.01 to about ten percent, and then subjecting said contents to an elevated temperature of about 150° to about 250° C. and an elevated pressure of at least about 2200 pounds per square inch for about five minutes to about five hours, sufficient to convert methanol to a product predominating in aldehydes.

2. The process of claim 1 wherein said sterically constrained carbon-carbon bond can be an alkylene bond, an arylene bond or an acetylenic bond.

3. The process of claim 1 wherein said sterically constrained carbon-carbon bond is an alkylene bond.

4. The process of claim 1 wherein said sterically constrained carbon-carbon bond is an arylene bond.

5. The process of claim 1 wherein said sterically constrained carbon-carbon bond is an acetylenic bond.

6. The process of claim 1 wherein said sterically constrained bond is incorporated into an alicyclic ring system.

7. The process of claim 1 wherein the molar ratio of carbon monoxide to hydrogen is in the range of about 1.5:1 to about 1:1.5, the molar ratio of cobalt to said ligand is in the range of about 1:1.5 to about 4:1, the molar ratio of cobalt to iodine is in the range of about 1:1.25 to about 1:5, and the weight percent of combined cobalt and iodine, based on the methanol, is in the range of about 0.1 to about five percent, and then subjecting said contents to an elevated temperature of about 170° to about 220° C. and an elevated pressure of about 2500 to about 7500 pounds per square inch gauge for about ten minutes to about 2.5 hours, sufficient to convert methanol to a product predominating in aldehydes.

8. The process of claim 7 wherein the molar ratio of carbon monoxide to hydrogen is in the range of about 1.25:1 to about 1:1.25.

9. The process of claim 1 wherein the ligand is defined by the following formula:

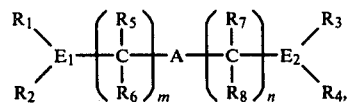

wherein $R_1$, $R_2$, $R_3$ and $R_4$ are either alike or different members selected from the group consisting of alkyl radicals having from one to 24 carbon atoms, aryl radicals having from six to 20 carbon atoms, alkenyl radicals having from two to 30 carbon atoms, cycloalkyl radicals having from three to 40 carbon atoms, and aralkyl and alkaryl radicals having from six to 40 carbon atoms; $R_5$, $R_6$, $R_7$ and $R_8$ are either alike or different members selected from the group consisting of hydrogen alkyl radicals having from one to 24 carbon atoms, aryl radicals having from six to 20 carbon atoms, alkenyl radicals having from two to 30 carbon atoms, cycloalkyl radicals having from three to 40 carbon atoms, and aralkyl and alkaryl radicals having from six to 40 carbon atoms; $E_1$ and $E_2$ are phosphorus atoms; A is an organic divalent radical in which the radical centers are located on adjacent carbon atoms and in which the bond axis of these adjacent carbon atoms is inhibited from rotating by bond unsaturation; and m and n are integers ranging from 0 to 2, provided that m+n is equal to 0 to 4.

10. The process of claim 9 wherein $R_1$, $R_2$, $R_3$ and $R_4$ are either alike or different members selected from the group consisting of alkyl radicals having from two to ten carbon atoms, aryl radicals having from six to ten carbon atoms, alkenyl radicals having from two to 20 carbon atoms, cycloalkyl radicals having from three to 30 carbon atoms, and aralkyl and alkaryl radicals having from six to 30 carbon atoms; and $R_5$, $R_6$, $R_7$ and $R_8$ are either alike or different members selected from the group consisting of hydrogen, alkyl radicals having from two to ten carbon atoms, aryl radicals having from six to ten carbon atoms, alkenyl radicals having from two to 20 carbon atoms, cycloalkyl radicals having from three to 30 carbon atoms; and aralkyl and alkaryl radicals having from six to 30 carbon atoms.

11. The process of claim 9 wherein said bond unsaturation has from two to ten carbon atoms.

12. The process of claim 9 wherein said bond unsaturation has from two to six carbon atoms.

13. The process of claim 9 wherein said bond unsaturation is an alkylene bond.

14. The process of claim 9 wherein said bond unsaturation is an arylene bond.

15. The process of claim 9 wherein said bond unsaturation is an acetylenic bond.

16. The process of claim 9 wherein said bond unsaturation is incorporated into an alicyclic ring system.

17. The process of claim 9 wherein $R_1$, $R_2$, $R_3$ and $R_4$ can be aryl or alkyl radicals.

18. The process of claim 9 wherein $R_1$, $R_2$, $R_3$ and $R_4$ are aryl radicals.

19. The process of claim 9 wherein $R_1$, $R_2$, $R_3$ and $R_4$ are alkyl radicals.

20. The process of claim 10 wherein $R_1$, $R_2$, $R_3$ and $R_4$ are aryl or alkyl radicals.

21. The process of claim 10 wherein $R_1$, $R_2$, $R_3$ and $R_4$ are aryl radicals.

22. The process of claim 10 wherein $R_1$, $R_2$, $R_3$ and $R_4$ are alkyl radicals.

23. The process of claim 10 wherein $R_5$, $R_6$, $R_7$ and $R_8$ can be hydrogen or aryl or alkyl radicals.

24. The process of claim 10 wherein $R_5$, $R_6$, $R_7$ and $R_8$ are hydrogen.

25. The process of claim 10 wherein $R_5$, $R_6$, $R_7$ and $R_8$ are aryl radicals.

26. The process of claim 10 wherein $R_5$, $R_6$, $R_7$ and $R_8$ are alkyl radicals.

27. The process of claim 10 wherein $R_1$, $R_2$, $R_3$ and $R_4$ are phenyl radicals and $R_5$, $R_6$, $R_7$ and $R_8$ are hydrogen.

28. The process of claim 9 wherein m and n are equal to 0, $R_1$, $R_2$, $R_3$ and $R_4$ are phenyl and A is ethylene.

29. The process of claim 10 wherein m and n are equal to 0, $R_1$, $R_2$, $R_3$ and $R_4$ are phenyl and A is ethylene.

30. The process of claim 9 wherein m and n are equal to 0, $R_1$, $R_2$, $R_3$ and $R_4$ are phenyl and A is phenyl.

31. The process of claim 10 wherein m and n are equal to 0, $R_1$, $R_2$, $R_3$ and $R_4$ are phenyl and A is phenyl.

32. The process of claim 9 wherein m and n are equal to 1, $R_1$, $R_2$, $R_3$ and $R_4$ are phenyl, $R_5$, $R_6$, $R_7$ and $R_8$ are hydrogen and A is phenyl.

33. The process of claim 10 wherein m and n are equal to 1, $R_1$, $R_2$, $R_3$ and $R_4$ are phenyl, $R_5$, $R_6$, $R_7$ and $R_8$ are hydrogen and A is phenyl.

34. The process of claim 9 wherein m and n are equal to 0, $R_1$, $R_2$, $R_3$ and $R_4$ are phenyl and A is acetylene.

35. The process of claim 10 wherein m and n are equal to 0, $R_1$, $R_2$, $R_3$ and $R_4$ are phenyl and A is acetylene.

* * * * *